(12) United States Patent
Bouman

(10) Patent No.: US 8,172,884 B2
(45) Date of Patent: May 8, 2012

(54) BONE PLATE WITH AT LEAST TWO ELONGATE HOLES AND BONE PLATE SYSTEM

(75) Inventor: Hans-Werner Bouman, Heidelberg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 1186 days.

(21) Appl. No.: 11/548,380

(22) Filed: Oct. 11, 2006

(65) Prior Publication Data

US 2007/0233114 A1    Oct. 4, 2007

Related U.S. Application Data

(60) Provisional application No. 60/726,945, filed on Oct. 14, 2005.

(30) Foreign Application Priority Data

Dec. 9, 2005   (DE) .................. 20 2005 019 277 U

(51) Int. Cl.
   *A61F 2/30*   (2006.01)
(52) U.S. Cl. ....................................... 606/280
(58) Field of Classification Search ............ 606/69, 606/70, 71, 60, 246–279, 280–299
   See application file for complete search history.

(56) References Cited

U.S. PATENT DOCUMENTS

| | | | | |
|---|---|---|---|---|
| 4,867,144 A | * | 9/1989 | Karas et al. ................... | 606/280 |
| 5,066,296 A | | 11/1991 | Chapman et al. | |
| 5,779,706 A | * | 7/1998 | Tschakaloff ................... | 606/281 |
| 6,221,073 B1 | * | 4/2001 | Weiss et al. ..................... | 606/60 |
| 6,506,191 B1 | * | 1/2003 | Joos ............................ | 606/86 B |
| 6,623,486 B1 | * | 9/2003 | Weaver et al. ................. | 606/281 |
| 6,652,530 B2 | * | 11/2003 | Ip et al. ......................... | 606/284 |
| 6,767,351 B2 | * | 7/2004 | Orbay et al. ................... | 606/287 |
| 7,112,202 B2 | * | 9/2006 | Michelson ....................... | 606/71 |
| 7,306,605 B2 | * | 12/2007 | Ross ............................... | 606/70 |
| 7,316,687 B2 | * | 1/2008 | Aikins et al. .................... | 606/70 |
| D580,058 S | * | 11/2008 | Simons ......................... | D24/155 |
| 2002/0143328 A1 | * | 10/2002 | Shluzas et al. .................. | 606/61 |
| 2004/0102775 A1 | * | 5/2004 | Huebner ......................... | 606/69 |
| 2004/0102778 A1 | * | 5/2004 | Huebner et al. ................. | 606/71 |
| 2004/0186356 A1 | * | 9/2004 | O'Malley et al. ............. | 600/231 |
| 2005/0137596 A1 | * | 6/2005 | Uwaydah ........................ | 606/69 |

FOREIGN PATENT DOCUMENTS

| | | |
|---|---|---|
| DE | G9001114.7 | 6/1990 |
| FR | 2556583 | 6/1985 |

* cited by examiner

*Primary Examiner* — Thomas C. Barrett
*Assistant Examiner* — Christopher Beccia
(74) *Attorney, Agent, or Firm* — Howard & Howard Attorneys PLLC

(57) ABSTRACT

A bone plate particularly suited for fractures that require the intraoperative correction in rotational and lengthwise axis described. The bone plate comprises a first, linear plate portion having a longitudinal axis and a first elongate hole extending in a direction of the longitudinal axis. The bone plate further comprises at least one second plate portion which extends substantially perpendicularly to the first plate portion. The second plate portion comprises a second elongate hole which extends roughly perpendicularly to the first elongate hole.

16 Claims, 5 Drawing Sheets

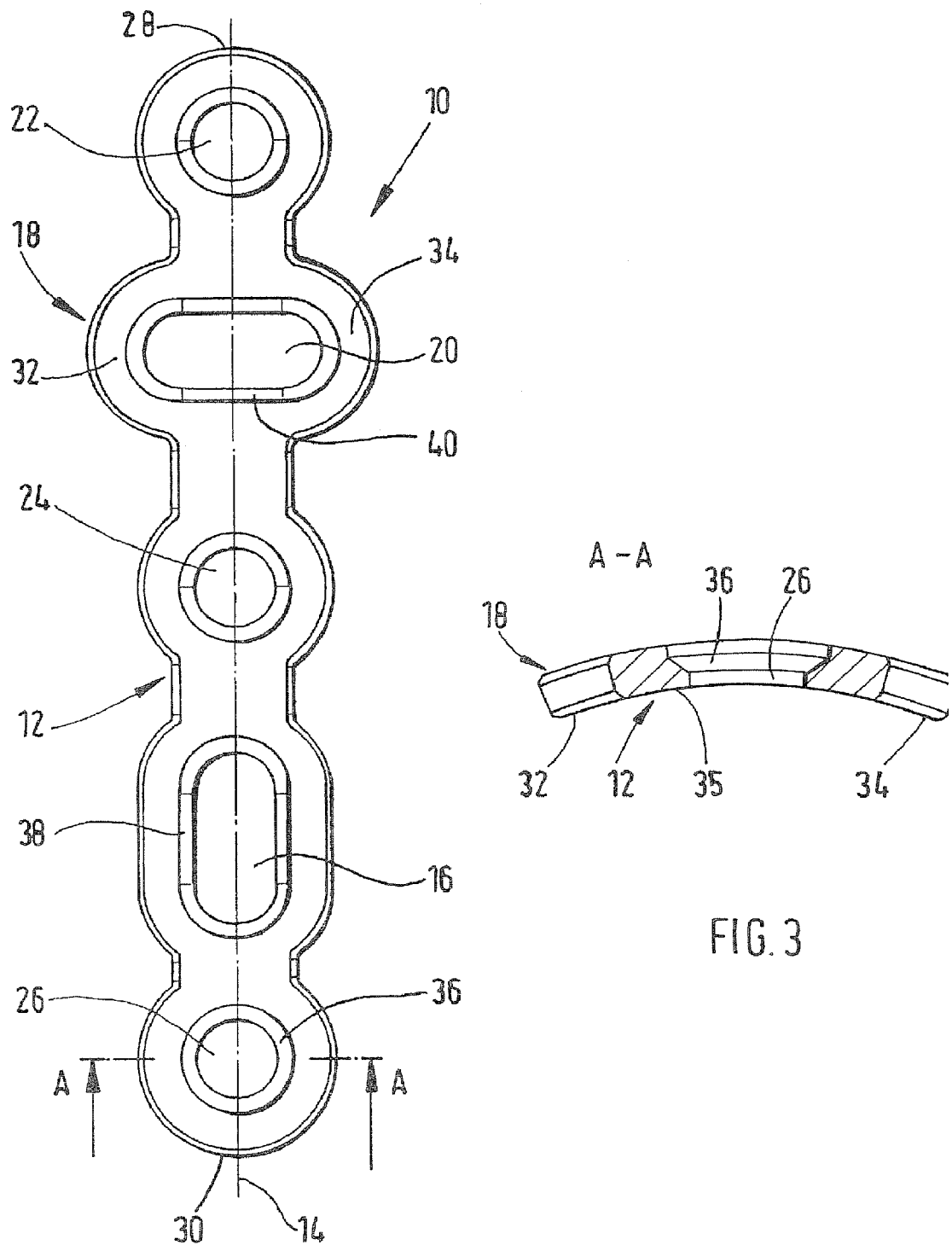

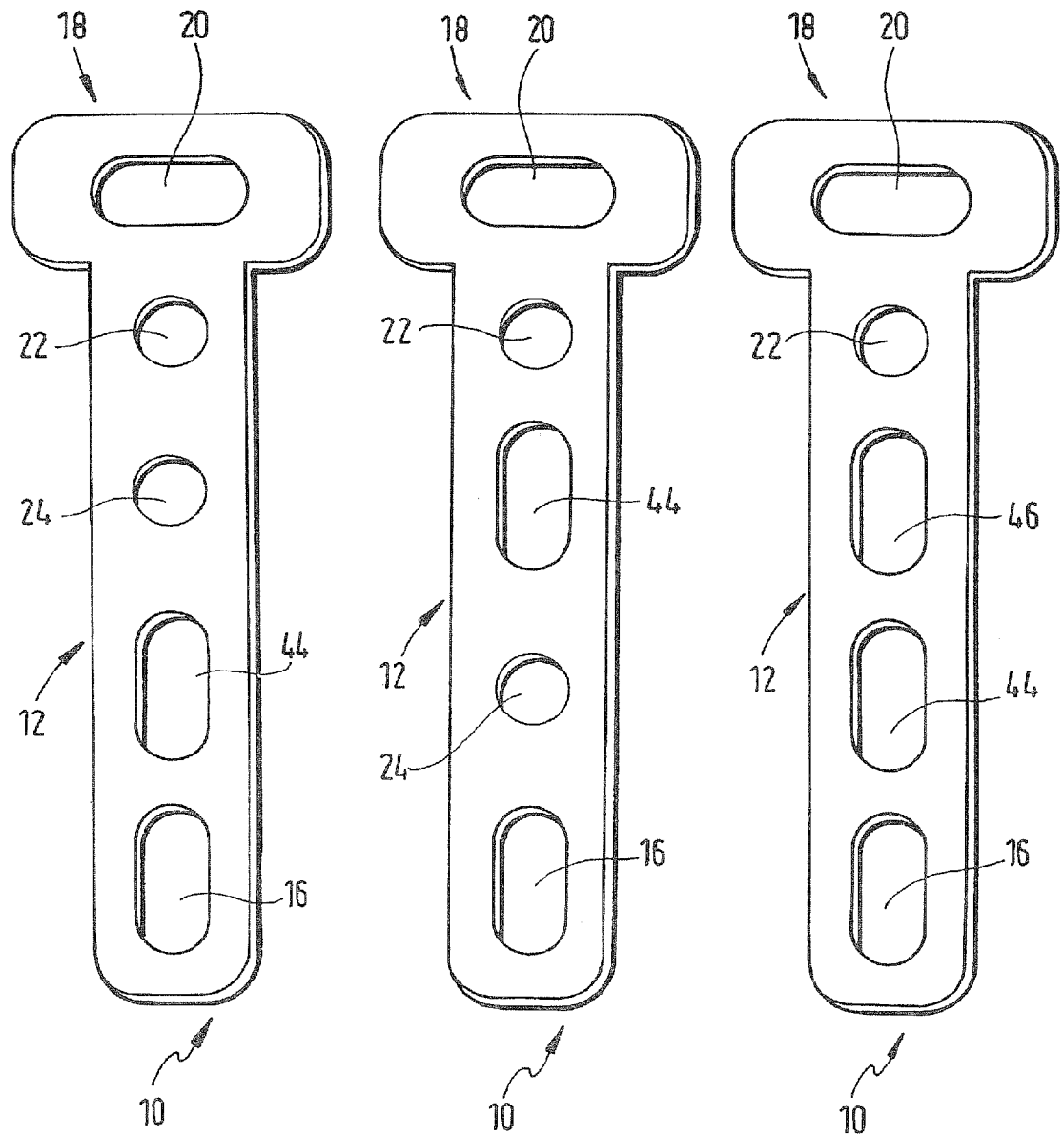

BONE PLATE WITH AT LEAST TWO ELONGATE HOLES AND BONE PLATE SYSTEM

RELATED APPLICATIONS

This application claims the benefit of U.S. Provisional Patent Application Ser. No. 60/726,945, filed Oct. 14, 2005, the advantages and disclosure of which are hereby incorporated by reference. This application also claims priority to German Utility Model Application No. 20 2005 019 277.5, filed Dec. 9, 2005.

TECHNICAL FIELD

The invention relates generally to devices for osteosynthesis. In particular, the invention is directed towards a bone plate with at least two elongate holes and to a bone plate system comprising this bone plate.

BACKGROUND OF THE INVENTION

Bone plates have been used for over 100 years to treat fractures. As a rule, bone plates have two or more passage openings for fastening elements, in order to ensure reliable fastening of the bone plates to the bones or bone fragments to be treated.

Many bone plates have circular passage openings. The diameter of a circular passage opening is often matched to the stem diameter of the fastening element to be introduced into the passage opening. In this way it is ensured that the bone plate is stably fastened to the bone or bone fragment, by reducing as far as possible translational relative motion between fastening element and bone plate within the plate plane.

Some bone plates have a passage opening in the form of an elongate hole. Elongate holes are often used if the plate is firstly to be fixed provisionally to a bone prior to final fixing. A fastening element which has been introduced provisionally into the elongate hole then ensures a degree of initial fixing of the bone plate, but at the same time allows repositioning to a certain extent of the only provisionally fixed bone plate.

The object of the present invention is to propose a bone plate which allows advantageous treatment of fractures while providing improved possibilities for in particular intraoperative correction.

SUMMARY OF THE INVENTION

This object is achieved by a bone plate with a first, linear plate portion and at least one second plate portion extending substantially perpendicularly to the first plate portion. The first plate portion has a longitudinal axis and a first elongate hole extending substantially in the direction of the longitudinal axis. In the second plate portion there is formed a second elongate hole, which extends substantially perpendicularly to the first elongate hole.

The length of the second plate portion may be defined roughly by the length of the second elongate hole. In other words, the second plate portion may extend perpendicularly to the first plate portion by an amount corresponding roughly to the length of the second elongate hole.

Preferably, the width of the bone plate is defined by the length of the second plate portion extending perpendicularly to the first plate portion. The length of the second plate portion may be many times smaller than the length of the first plate portion. In one embodiment, the length of the second plate portion amounts to less than roughly twice the maximum width of the first plate portion. Although the length of the second plate portion may in principle also correspond to the maximum width of the first plate portion, in one preferred embodiment the second plate portion projects beyond the maximum width of the first plate portion.

The second plate portion may be provided roughly in a head region of the first plate portion. According to a further development of this arrangement, the first plate portion and the second plate portion are arranged relative to one another roughly in the shape of a T. If two or more second plate portions are to be provided, the second plate portions may be distributed over the length of the first plate portion.

It has proven convenient to arrange the second elongate hole roughly centrally relative to the longitudinal axis. In this case, the longitudinal axis thus divides the second elongate hole into two halves of roughly equal size. Between the first elongate hole and the second elongate hole it is possible to arrange at least one circular passage opening. Such a circular passage opening may also be provided between a first end region of the first plate portion remote from the second plate portion and the first elongate hole. It is additionally feasible to arrange a circular passage opening between a second end region of the first plate portion adjacent the second plate portion and the second elongate hole.

The bone plate may be provided with a total of three, four or still more elongate holes. In one embodiment with at least three elongate holes, a third elongate hole may be arranged offset relative to the first elongate hole along the longitudinal axis.

According to a first variant, the third elongate hole extends parallel to the first elongate hole. According to a second variant, the third elongate hole extends perpendicularly to the first elongate hole.

The bone plate may comprise rectilinear boundary zones at its outer periphery or consist of individual members in the manner of a chain. Preferably, each plate member comprises exactly one elongate hole and/or exactly one circular passage opening.

According to a first option, the bone plate is planar in form. According to a second option, the bone plate has a non-planar, curved form, for instance in the manner of a cylinder jacket portion. The bone plate may have a curvature conformed to a bone radius in a plane extending perpendicularly to the longitudinal axis.

The length of the first plate portion may be selected differently depending on the indication. Thus, it is feasible for the first plate portion to exhibit a length of less than roughly 200 mm (for example of less than roughly 50 mm). As far as the second plate portion is concerned, a length of less than roughly 50 mm (for example of less than roughly 20 mm) is feasible. The bone plate thickness amounts typically to less than roughly 5 mm and lies preferably in a range of between roughly 0.5 and 3 mm. Each of the elongate holes may exhibit a length of up to 25 mm. In one preferred development of the invention, the length of the elongate holes amounts in each case to roughly 3 to 10 mm.

According to a further aspect of the invention, a bone plate system is provided which, in addition to the above-described bone plate, also comprises two or more fastening elements. A first fastening element is designed to slide in the first elongate hole and a second fastening element is designed to slide in the second elongate hole (at least when the two fastening elements are in the provisionally fastened state). The bone plate may moreover comprise a circular passage opening and at least one third fastening element, which may be introduced into the circular passage opening in such a manner as to be unable to perform a translational movement relative to a plate plane. The fastening elements may preferably comprise bone screws, but bone nails or Kirschner wires may also be used.

BRIEF DESCRIPTION OF THE DRAWINGS

Further aspects, variations and advantages of the invention are revealed by the following description of a preferred exemplary embodiment and by the Figures, in which:

FIG. 2 shows a plan view of the bone plate according to FIG. 1;

FIG. 3 shows a section along line A-A of the bone plate according to FIG. 2;

FIGS. 4 to 6 show three embodiments of bone plates with three or more elongate holes;

DESCRIPTION OF PREFERRED EMBODIMENTS

Figure 1:
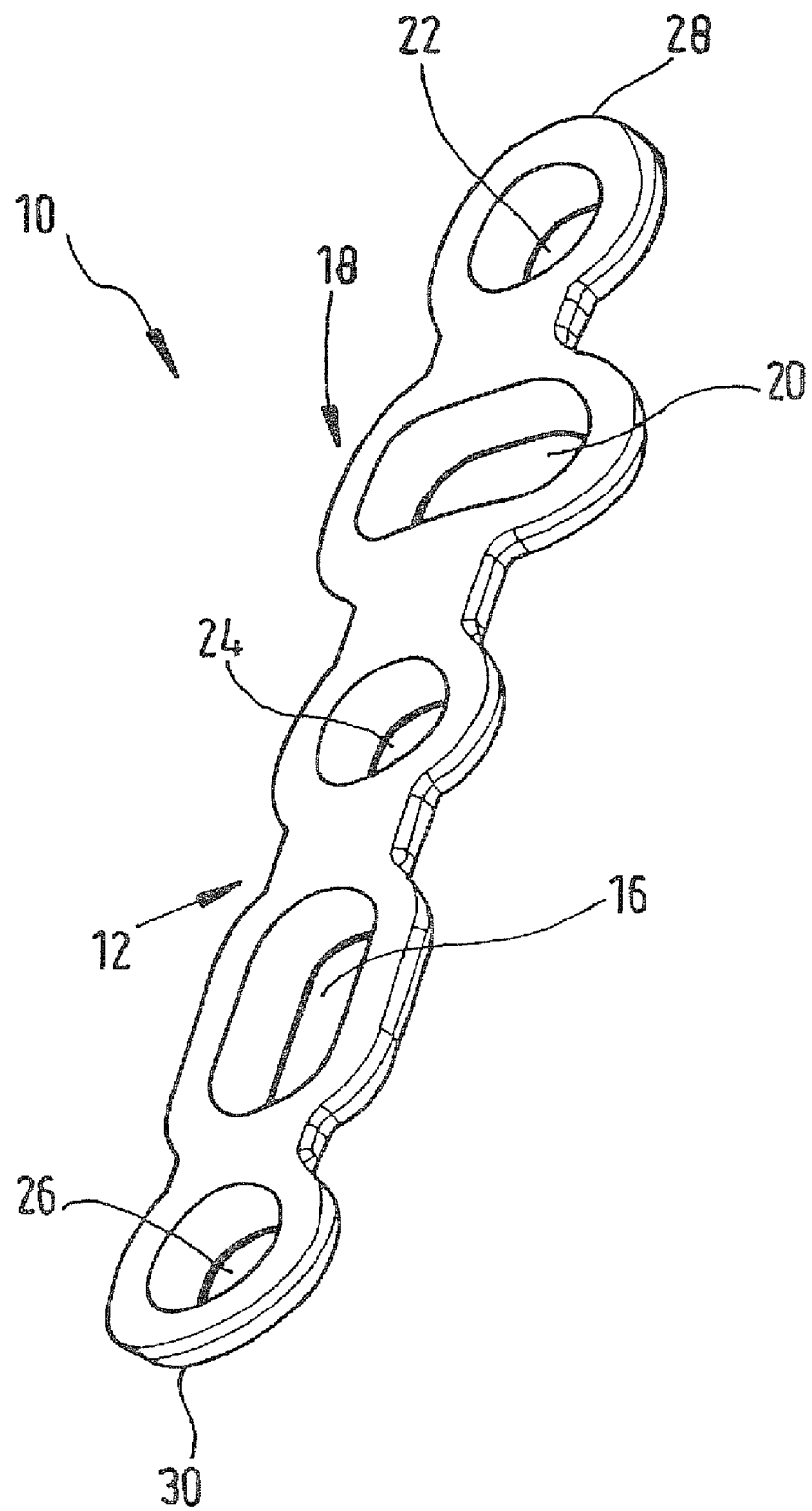
FIG. 1 shows a perspective view of a first embodiment of a bone plate according to the invention.

FIGS. 1 to 3 show a first embodiment of a bone plate 10. The bone plate 10 comprises a first, linear plate portion 12 consisting of a plurality of members and having a longitudinal axis 14 and a first elongate hole 16 extending in the direction of the longitudinal axis 14. The bone plate 10 additionally has a second plate portion 18, which extends perpendicularly to the first plate portion 12 and comprises a second elongate hole 20. The second elongate hole 20 extends perpendicularly to the first elongate hole 16.

In addition to the two elongate holes 16, 20, the bone plate 10 has a total of three circular passage openings 22, 24, 26. A first circular passage opening 22 is arranged between a first end region 28 of the first plate portion 12 adjacent the second plate portion 18 and the second elongate hole 20. A second circular passage opening 24 is provided between the first elongate hole 16 and the second elongate hole 20. A third passage opening 26 is formed between a second end region 30 of the first plate portion 12 remote from the second plate portion 18 and the first elongate hole 16.

As is particularly clear from FIG. 2, the second plate portion 18 is provided roughly in the end region 28 of the first plate portion 12. The bone plate 10 therefore takes overall a roughly T-shaped form, wherein the length of the second plate portion 18 is many times smaller than the length of the first plate portion 12, however. The length of the second plate portion 18 amounts to markedly less than twice the maximum width (for example in the region of the first passage opening 22) of the first plate portion 12. It should be noted, in this respect, that the length of the second plate portion 18 is substantially determined by the length of the second elongate hole 20. This means here that the length of the second plate portion 18 exceeds the length of the second elongate hole 20 solely by the thickness of the two bulging boundary zones 32, 34 of the second elongate hole 20.

According to the cross-section of the bone plate 10 shown in FIG. 3 and taken along line A-A in FIG. 2, the passage opening 26 (just like the passage openings 22 and 24) has a diameter which tapers step-wise towards the plate underside 35. A conical seating portion 36 of the passage opening 26 serves as bearing surface for the head of a fastening element introduced into the passage opening 26. The two elongate holes 16, 20 have similar seating surfaces with straight portions 38, 40 (FIG. 2) extending parallel to the longitudinal axis, the significance of which will be explained in greater detail below in connection with FIGS. 9A and 9B.

As is additionally clear from FIG. 3, the bone plate 10 is curved in a plane extending perpendicularly to the longitudinal axis 14. This curvature of the bone plate 10 is conformed to the bone radius, which forms the basis of the indication of the bone plate 10, and amounts in the exemplary embodiment to roughly 10 mm. Unlike in FIG. 3, the bone plate 10 could also be of completely planar construction.

In the embodiment, the length of the first portion 12 of the bone plate amounts to roughly 35 mm, the length of the second plate portion 18 (measured perpendicularly to the longitudinal axis 14) to roughly 8 mm, the length of each of the two elongate holes 16, 18 to roughly 5 mm and the thickness of the bone plate 10 to roughly 1 mm. Depending on the indication, these dimensions may also be larger or smaller.

FIGS. 4 to 8 show further embodiments of bone plates 10. Corresponding elements are provided with the same reference numerals as in the first exemplary embodiments explained with reference to FIGS. 1 to 3.

The bone plates 10 illustrated in FIGS. 4 to 6 have a markedly more pronounced T-shape than the bone plate of the first exemplary embodiment, due to the fact that the respective second plate portion 18 directly adjoins the end region of the respective first plate portion 12. Unlike in the first exemplary embodiment, the bone plates 10 of FIGS. 4 to 6 comprise two (FIGS. 4 and 5) or three (FIG. 6) elongate holes 16, 44, 46 in the first plate portion 12. The further elongate holes 44, 46 of the first plate portion 18 extend along the respective longitudinal plate axis (not shown) and thus parallel to the first elongate hole 16. In comparison to the bone plate of the first embodiment, the bone plates 10 each have only two passage openings 22, 24 (FIGS. 5 and 6) or only one passage opening 22 (FIG. 6).

Figure 8:
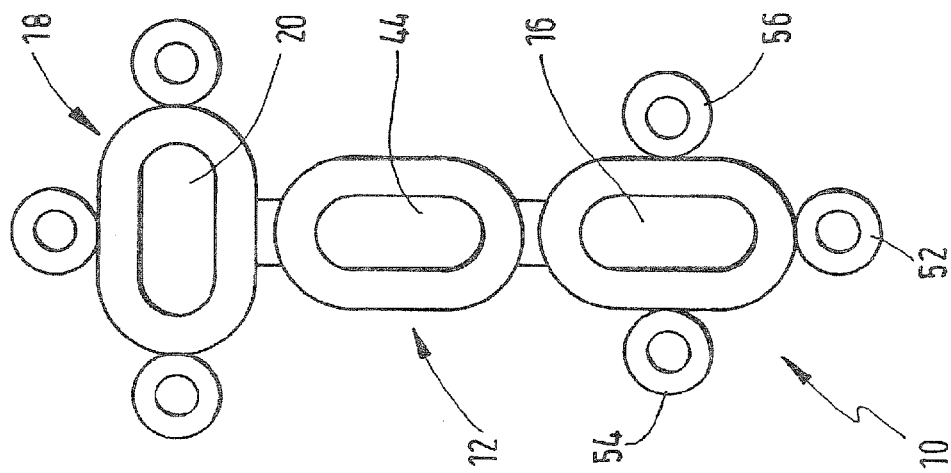
FIGS. 7 and 8 show two embodiments of bone plates having individual plate members.
Figure 7:
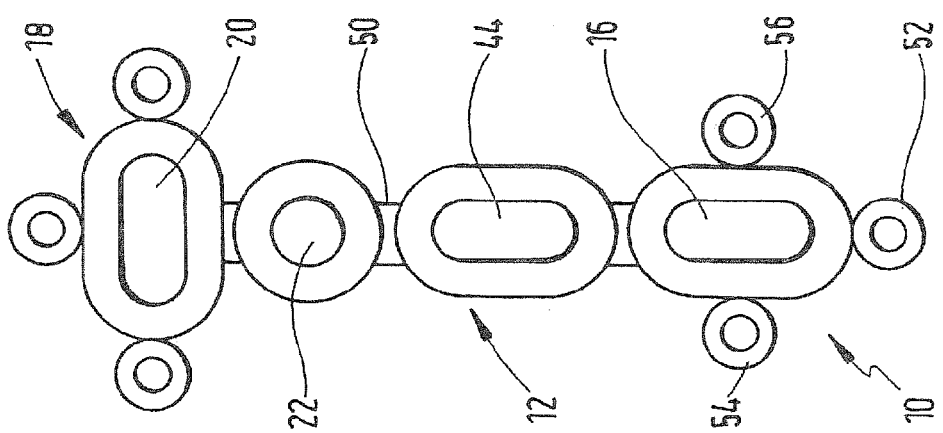

FIGS. 7 to 8 show two further embodiments of bone plates 10. Each of these bone plates 10 consists of individual annular members, which are coupled together directly or by means of short webs 50.

The bone plate 10 according to FIG. 7 has a first plate portion 12, which is formed substantially of two elongate hole members (elongate holes 16 and 44) and a member with a circular passage opening 22. At the outer periphery of the lowermost elongate hole member in FIG. 7 there are provided three smaller members 52, 54, 56, each with a circular passage opening. The member with the elongate hole 20, which is arranged in the head region of the first plate portion 12 and forms the second plate portion 18, is also provided at its outer periphery with three corresponding members. The internal diameters of the passage openings of the members 52, 54, 56 are smaller than the diameter of the passage opening 22 of the member arranged in the first plate portion 12. The passage openings 52, 54, 56 serve to receive fastening elements of smaller diameter or surgical wires.

The bone plate 10 according to FIG. 8 corresponds substantially to the bone plate 10 illustrated in FIG. 7. However, it has a shorter first plate portion 12, since the member with the circular passage opening 22 has been omitted.

Figure 9A:
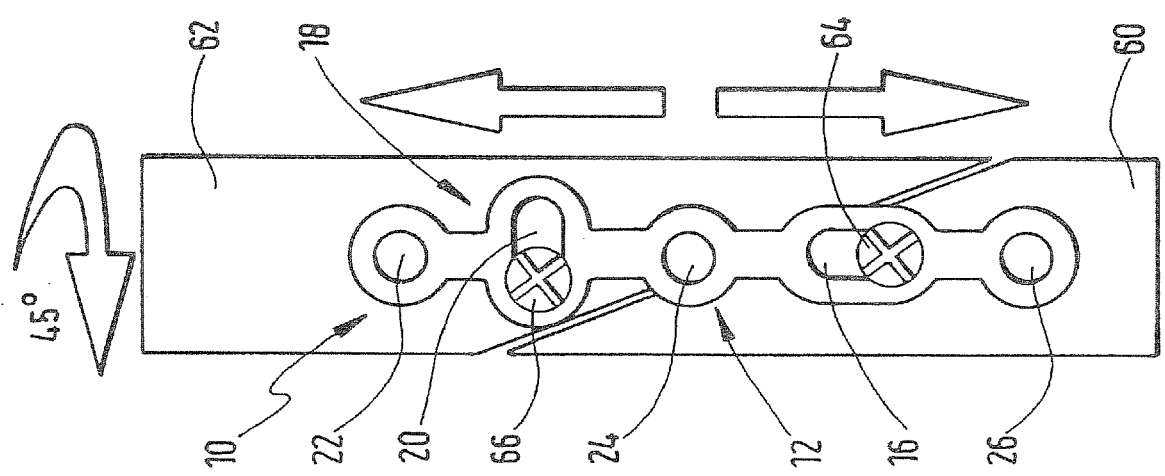
FIGS. 9A and 9B show an embodiment of surgical use of the embodiment of the bone plate illustrated in FIGS. 1 to 3.
Figure 9B:
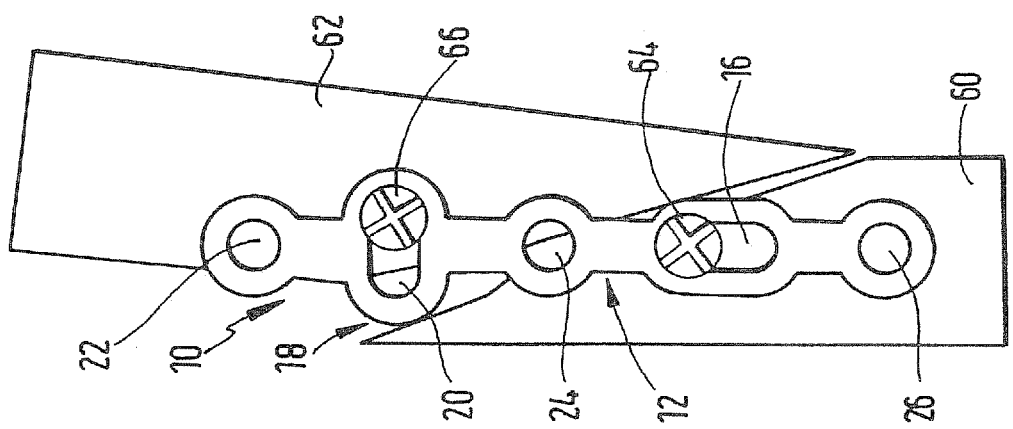

A possible surgical use of the bone plate 10 illustrated in FIGS. 1 to 3 will now be explained with reference to FIGS. 9A and 9B. The exemplary embodiment relates to the treatment of fractures in the area of the hand, in particular to oblique fractures of phalanges or metacarpal bones. In such a case it was hitherto difficult to achieve exact restoration of the anatomical position, since the corresponding bone fragments are small and the nerves, blood vessels and ligaments present in the hand area make it essential to proceed extremely carefully.

The bone plates used hitherto in the treatment of fractures of the phalanges and metacarpal bones frequently did not allow completely satisfactory fracture treatment. Inadequate fracture treatment of the phalanges and metacarpal bones often results in loss of length and/or rotation. A finger may then for example be too short, at an angle or twisted after completion of treatment. This is undesirable for both aesthetic and functional reasons.

The bone plates 10 each with two mutually perpendicular elongate holes 16, 20 explained with reference to the exemplary embodiments have proven suitable for better treatment of fractures, in particular in the case of oblique fractures and in particular in the region of the phalanges and metacarpal bones. This is explained hereinafter for the bone plate 10 of the first embodiment (FIGS. 1 to 3) and with reference to the treatment of an oblique fracture of a phalanx illustrated in FIGS. 9A and 9B.

In a first step (not shown), provisional repositioning of the two bone fragments 60, 62 takes place, with the assistance of a reduction clamp. In a second step (FIG. 9A), the bone plate 10 is provisionally fastened to the two repositioned fragments 60, 62. To this end, a first fastening element in the form of a bone screw 64 is passed through the first elongate hole 16 and provisionally fastened to the fragment 60. A second fastening element in the form of a further bone screw 66 is passed through the elongate hole 20 and provisionally fastened to the second bone fragment 62. When fastening the bone screw 64, care should be taken to ensure that it is arranged in the elongate hole 16 as close as possible relative to the second plate portion 18, so as to allow the provisionally fastened plate 10 in FIG. 9A to slide upwards. Depending on the type of malrotation between the two bone fragments 60, 62, the second bone screw 66 should be arranged in one of the two end regions of the elongate hole 20 in such a way that the bone plate 10 may slide to the left or right relative to the bone screw 66. In the case of the fracture illustrated in FIG. 9A, it is convenient to provide the bone screw 66 in the right-hand end region of the elongate hole 20.

Once the bone plate 10 has been provisionally fastened (preferably loosely) by means of the bone screws 64, 66 to the fragments 60, 62, more exact repositioning of the bone fragments 60, 62 is effected (as illustrated by the arrows in FIG. 98) by turning the bone fragment 62 and/or by bringing the two bone fragments 60, 62 together translationally. During this repositioning, the bone screws 64, 66 slide within the elongate holes 16, 20 into their final position. The elongate holes 16, 20 thus function in this case as "slideways" with regard to the bone screws 64, 66. The sliding movement of the bone screws 64, 66 in the elongate holes 16, 18 is assisted by the seating surfaces 38, 40 of the elongate holes 16, 20 shown in FIG. 2.

After final repositioning of the two bone fragments 60, 62, depending on the fracture, typically the bone screw 64 is firstly tightened reliably in the elongate hole 16 extending parallel to the longitudinal axis of the bone plate 10. Then, any remaining malrotation may be corrected by relative motion between the bone screw 66 and the bone plate 10, before the bone screw 66 is also finally tightened. If necessary, the bone screw 64 may then be slightly loosened again for optimum repositioning, the two bone fragments 60, 62 again moved relative to one another and then the bone screw 64 tightened again.

After satisfactory repositioning and reliable fastening of the two bone screws 64, 66, further fastening screws (not shown) are introduced into one or more of the passage openings 22, 24 and 26 for final fixing of the bone plate 10.

The above-described fracture treatment by means of the bone plate 10 consequently does not require complete repositioning of the bone plate 10 if it becomes necessary to change the position of a bone fragment 60, 62 during fixing of the screws 64, 66. Instead, such changes in position may be compensated by means of the elongate holes 16, 20. The elongate holes 16, 20 additionally function as slideways for the provisionally fastened bone screws 64, 66, which advantageously assist in repositioning of the bone fragments 60, 62 (FIG. 9B).

It is obvious to the person skilled in the art that the bone plates described with reference to the exemplary embodiments are particularly suitable for the treatment of fractures, in particular of oblique fractures, in the area of the hand. Nonetheless, the bone plates may also be used to treat other fractures, for example in the area of the foot. Use to treat fractures in the leg or arm area is also possible if appropriately dimensioned bone plates are used.

Although the preferred embodiments of the present invention have been described and illustrated in detail, it will be evident to those skilled in the art that various modifications and changes may be made thereto without departing from the spirit and scope of the invention as set forth in the appended claims and equivalents thereof.

What is claimed is:

1. A bone plate, comprising:
   a first, linear plate portion having a longitudinal axis and a first elongate hole extending in a direction of the longitudinal axis, the first plate portion extending between a first end and a second end; and
   a second plate portion, which extends substantially perpendicularly to the first plate portion, wherein the second plate portion comprises a second elongate hole, which extends roughly perpendicularly to the first elongate hole;
   the first plate portion and the second plate portion being arranged crosswise, wherein the first plate portion comprises at least one first circular passage opening arranged between the first end and the second elongate hole and at least one second circular passage opening arranged between the second end and the first elongate hole,
   the first circular passage opening being located adjacent the second elongate hole and the second circular passage opening being located remote from the second elongate hole such that the first elongate hole is arranged between the second elongate hole and the second circular passage opening.

2. The bone plate according to claim 1, wherein the length of the second plate portion is substantially determined by the length of the second elongate hole.

3. The bone plate according to claim 1, wherein the length of the second plate portion amounts to less than roughly twice the maximum width of the first plate portion.

4. The bone plate according to claim 1, wherein the second elongate hole is arranged roughly centrally relative to the longitudinal axis.

5. The bone plate according to claim 1, wherein at least one circular passage opening is arranged between the first elongate hole and the second elongate hole.

6. The bone plate according to claim 1, wherein at least one third elongate hole is provided in the first plate portion, which third hole is arranged between the first elongate hole and the second elongate hole along the longitudinal axis and extends parallel to the longitudinal axis.

7. The bone plate according to claim 1, wherein the bone plate includes individual members, wherein each member comprises precisely one elongate hole or precisely one circular passage opening.

8. The bone plate according to claim 1, wherein the bone plate exhibits a curvature conformed to a bone radius in a plane extending perpendicularly to the longitudinal axis.

9. The bone plate according to claim 1, wherein the first plate portion exhibits a length of less than roughly 50 mm.

10. The bone plate according to claim 1, wherein the second plate portion exhibits a length of less than roughly 20 mm.

11. The bone plate according to claim 1, wherein the thickness of the bone plate amounts to roughly 0.5 to 3 mm.

12. The bone plate according to claim 1, wherein at least one the elongate holes exhibits a length of roughly 3 to 10 mm.

13. A bone plate system, comprising
a bone plate having a first, linear plate portion with a longitudinal axis and a first elongate hole extending in a direction of the longitudinal axis, the first plate portion extending between a first end and a second end;
a second plate portion, which extends substantially perpendicularly to the first plate portion, the second plate portion comprising a second elongate hole, which extends roughly perpendicularly to the first elongate hole, wherein the first plate portion and the second plate portion are arranged crosswise, wherein the first plate portion comprises at least one first circular passage opening arranged between the first end and the second elongate hole and at least one second circular passage opening arranged between the second end and the first elongate hole, the first circular passage opening being located adjacent the second elongate hole and the second circular passage opening being located remote from the second elongate hole such that the first elongate hole is arranged between the second elongate hole and the second circular passage opening;
a first fastening element, which is designed to slide in the first elongate hole; and
a second fastening element, which is designed to slide in the second elongate hole.

14. The bone plate system according to claim 13, wherein the bone plate comprises at least one third fastening element, which may be introduced into one of the circular passage openings in such a manner as to be unable to effect translational movement relative to a plate plane.

15. A method of treating a fractured bone, comprising:
providing a bone plate having a first, linear plate portion having a longitudinal axis and a first elongate hole extending in a direction of the longitudinal axis, the first plate portion extending between a first end and a second end;
a second plate portion, which extends substantially perpendicularly to the first plate portion, the second plate portion comprising a second elongate hole, which extends roughly perpendicularly to the first elongate hole, wherein the first plate portion and the second plate portion are arranged crosswise, and the first plate portion comprises at least one first circular passage opening arranged between the first end and the second elongate hole and at least one second circular passage opening arranged between the second end and the first elongate hole, the first circular passage opening being located adjacent the second elongate hole and the second circular passage opening being located remote from the second elongate hole such that the first elongate hole is arranged between the second elongate hole and the second circular passage opening;
provisionally fastening the bone plate to the fractured bone by placing a first bone screw in the first elongate hole and a second bone screw in the second elongate hole in such a manner as to allow each of the two bone screws a sliding movement within the respective elongate hole;
tightening a first one of the first and second bone screws;
correcting any rotation failure by adjusting the position of the other one of the first and second bone screws in the respective elongate hole; and
tightening the other one of the first and second bone screws.

16. The method of claim 15, further comprising:
slightly loosening one of the first and second bone screws;
adjusting the position of the loosened bone screw within the respective elongate hole for a further adjustment of the bone fragments; and
tightening the loosened bone screw.

* * * * *